United States Patent [19]
Swaelens et al.

[11] Patent Number: 5,595,703
[45] Date of Patent: Jan. 21, 1997

[54] METHOD FOR SUPPORTING AN OBJECT MADE BY MEANS OF STEREOLITHOGRAPHY OR ANOTHER RAPID PROTOTYPE PRODUCTION METHOD

[75] Inventors: Bart Swaelens, Putte; Johan Pauwels, Bornem; Wilfried Vancraen, Huldenberg, all of Belgium

[73] Assignee: Materialise, Naamloze Vennootschap, Belgium

[21] Appl. No.: 402,525

[22] Filed: Mar. 10, 1995

[30] Foreign Application Priority Data

Mar. 10, 1994 [BE] Belgium .................. 09400267

[51] Int. Cl.⁶ .................. B29C 35/08; B29C 41/02
[52] U.S. Cl. .................. 264/401; 156/272.8; 156/273.5; 156/275.5; 156/307.1; 264/308; 264/497; 427/510; 427/512; 427/553; 427/554; 427/555
[58] Field of Search .................. 264/236, 255, 264/308, 401, 497; 156/272.8, 273.3, 273.5, 275.5, 307.1; 427/508, 510, 512, 553, 554, 555

[56] References Cited

U.S. PATENT DOCUMENTS

| 5,198,159 | 3/1993 | Nakamura et al. | 264/401 |
| 5,362,427 | 11/1994 | Mitchell, Jr. | 264/497 |

FOREIGN PATENT DOCUMENTS

| 338751 | 10/1989 | European Pat. Off. . |
| 348061 | 12/1989 | European Pat. Off. . |
| 388129 | 9/1990 | European Pat. Off. . |
| 416124 | 3/1991 | European Pat. Off. . |
| 484183 | 5/1992 | European Pat. Off. . |
| 590957 | 4/1994 | European Pat. Off. . |
| 4125534 | 2/1993 | Germany . |
| 2-52725 | 2/1990 | Japan .................. 264/401 |
| WO89/10255 | 11/1989 | WIPO . |
| WO92/18323 | 10/1992 | WIPO . |
| WO92/20505 | 11/1992 | WIPO . |

OTHER PUBLICATIONS

Dipl.–Ing. S. Kegelmann, *Stereolithographie moglichkeiten und Grenzen*, 2297 Gummi, Fasern, Kuntststoffe, pp. 333–334 and 336, Jun. 1991.

J. Bisschop en J. C. Jagt, *Stereolithografie*, pp. 11–18, 1245 Kunststof en Rubber, Feb. 1992.

*Primary Examiner*—Leo B. Tentoni
*Attorney, Agent, or Firm*—Bacon & Thomas

[57] ABSTRACT

A method of supporting an object made by stereolithography or another rapid prototype production method, in which a support is provided with at least one supporting structure which is airier than a supporting structure made of solid standing walls, including those made with notches at the top and/or at the bottom. The supporting structure can be made airy by using walls of which at least a number are provided with openings over a major part of their surface.

13 Claims, 6 Drawing Sheets

METHOD FOR SUPPORTING AN OBJECT MADE BY MEANS OF STEREOLITHOGRAPHY OR ANOTHER RAPID PROTOTYPE PRODUCTION METHOD

BACKGROUND OF THE INVENTION

1. Field of the Invention

The invention concerns a method for supporting, at least with one supporting structure, an object made by means of stereolithography or another rapid prototype production method.

2. Discussion of the Prior Art

Stereolithography is a method known as such whereby a photopolymer is cured by means of electromagnetic rays, for example one or several laser beams which are computer-controlled. Due to the beams, the liquid photopolymer cures at the surface according to a specific pattern. The polymerized coat is usually anchored with the help of a supporting structure to a platform which, each time another coat is polymerized, sinks somewhat deeper in the liquid polymer. The supporting structure keeps the object in place during the production process and prevents deformations. Thus, the supporting structure and the object are built layer by layer. This form of stereolithography is described among others in U.S. Pat. No. 4.575.330 and EP-A-348.061.

The patterns with which pieces or objects are hardened by stereolithography or photopolymerized, have been subject to a lot of development. In different documents, optimizing of speed, of ligthening of structure and avoiding internal tensions are described for example in WO-A-89/10255, WO-A-92/20505 and EP-A-0590957. As to the support construction, the optimalization in light of the functional requirements is still very limited.

In the known stereolithography, this supporting structure is built in the shape of solid, standing walls which are usually connected to one another according to a pattern, such as described in EP-A-0338751. Especially with large objects, the building of this supporting structure requires much time, energy and material, so that this supporting structure makes the method relatively expensive. Indeed, the supporting structure is lost material. Moreover, when the object is finished, liquid material remains sticking against and in between these walls, which makes the loss of material even greater. Finally, it is often difficult to remove these solid walls from the object without damaging it or without leaving clear marks on the object.

Especially to avoid these last-mentioned disadvantages, it is already known to provide the walls with notches at the top and/or at the bottom. The notches at the top restrict the contact with the object and make it easier to remove the supporting structure. The notches also make sure that liquid polymer which is stuck between the walls under the object can flow away. However, they offer no solution for the large consumption of material of the supporting structure and the loss of liquid polymer which remains sticking against the walls, nor do they offer any gain of time.

Similar problems arise with supporting structures used for other rapid prototype production methods, generally called "rapid prototyping". Such other production methods or material growth techniques are for example other photopolymerization techniques which make use of a mask, a film, a coated glass plate or LCD plate; selective laser sintering; what is called fused deposition modelling; ink jet techniques and foil-based techniques.

With selective laser sintering of metal or plastic powders, the powder which is present in a support, which is removed afterwards, is sintered or welded with a laser or another focused heat source.

Fused deposition modelling and related techniques make use of a temporary transition from a solid material to a liquid state, usually due to heating. The material is driven through a nozzle in a controlled way and deposited in the required place as described among others in U.S. Pat. No. 5.141.680.

Foil-based techniques fix coats to one another by means of gluing or photopolymerization or other techniques and cut the object from these coats or polymerize the object. Such a technique is described in U.S. Pat. No. 5.192.559.

SUMMARY OF THE INVENTION

The invention aims to remedy the above-mentioned disadvantages and to provide a method for supporting an object made by means of stereolithography or any other rapid prototype production method which requires a minimum amount of material and allows for a faster production of the object than is possible with the usual supporting structures.

The aim is reached according to the invention by providing a supporting structure which is airier than a supporting structure made of solid standing walls and possibly notches at the top and/or at the bottom.

According to a first preferred embodiment, support is provided with a supporting structure which is airy because it is made of walls of which at least a number are provided with openings over a major part of their surface.

Practically, a supporting structure is supported which contains walls provided with openings which are erected according to a pattern whereby they cross or intersect. These walls may be both vertical or inclined, flat or bent. Where two walls cross, the openings are preferably situated such that they intersect at points where there is material in both walls.

Support can be provided with a supporting structure whose openings in the walls are so large that in fact merely bars remain which are interconnected by means of junctions.

According to a variant of this embodiment, support is provided with a supporting structure which contains bars which have a profile situated diagonally on their longitudinal direction. Instead of a line profile, the section of the bars can have any shape whatsoever, such as an L, a cross, a square, a rectangle, a circle or an ellipse.

Preferably, a supporting structure is used of which at least the raised edges of the walls do not have any openings.

According to another preferred embodiment, support is provided with a supporting structure which is airy because it is made of walls of which at least a number do not continue over the entire height of the supporting structure, but whereby the walls are situated further away from one another near the lower end of this supporting structure than in the proximity of the supported object.

Moreover, these walls can be provided with openings and thus, as in the first embodiment, they can even be replaced by bars. Towards the object, the bars are situated closer together.

According to yet another embodiment, support is provided with a supporting structure which is airy because it includes a set of hollow columns, in whose walls openings are provided.

These columns may have any open or closed section whatsoever and possibly, as in the first embodiment, be provided with one or several openings.

According to a special embodiment, support is provided with columns which widen at the bottom towards the object.

The above-mentioned embodiments to build an airy supporting structure can be made according to the same methods which are used to make the object which is supported, but special measures have to be taken into account to obtain the specific shape of the supporting structure. The supporting structures can be made with the help of standard CAD systems, on the basis of programs which automatically design the supporting structure and transcribe it in STL or another surface format which describes the spacial structure, on the basis of the above-mentioned techniques applied on structures with solid walls, but with additional software to obtain recesses according to a fixed pattern by logically processing images of for example scanners or by logically processing contours of a model and by shading the results according to a suited methodology.

BRIEF DESCRIPTION OF THE DRAWINGS

In order to better explain the characteristics of the invention, the following preferred embodiments of a method for supporting an object made by means of stereolithography or another rapid prototype production method are given as an example only without being limitative in any way, with reference to the accompanying drawings, in which.

DETAILED DESCRIPTION OF THE PREFERRED EMBODIMENT

Figure 1:
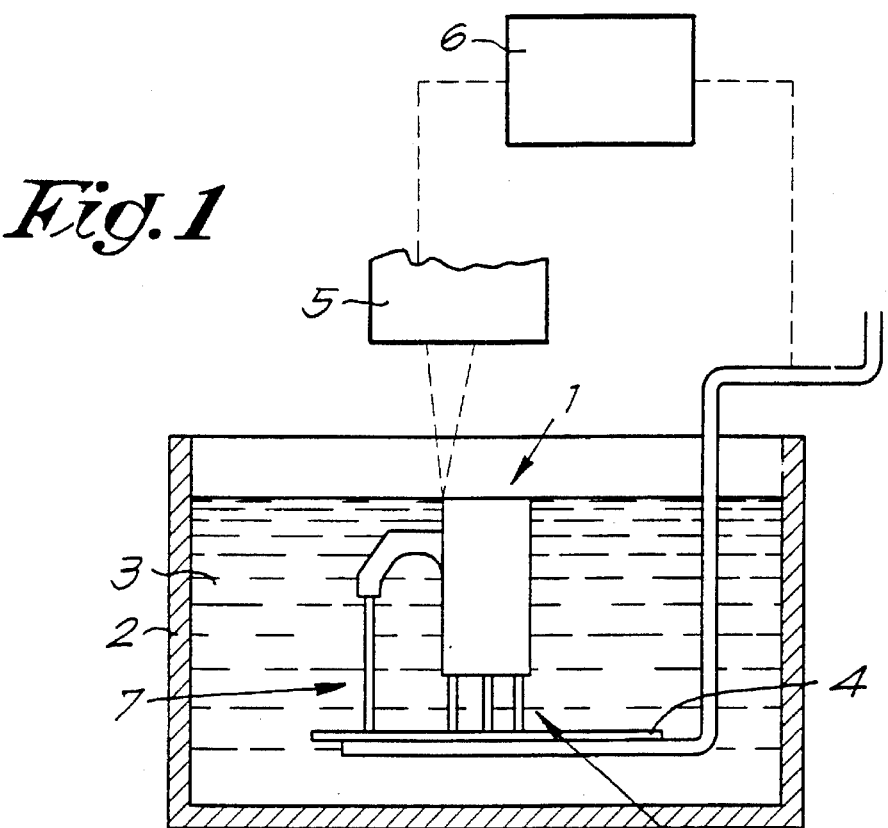
FIG. 1 is a schematic representation of a device for making an object by means of stereolithography whereby the object is supported with a supporting structure according to the invention.

The device represented in FIG. 1 for making an object 1 by means of stereolithography is of a design known as such. This device mainly contains a vessel 2 filled with a liquid prepolymer 3 which can be photopolymerized, a platform 4 erected therein which can be moved up and down in the liquid prepolymer by a mechanism which is not represented and a laser beam source 5 which can be moved over the surface of the liquid prepolymer 3 according to a specific pattern by a mechanism which is not represented either.

Both the mechanism for moving up and down the platform 4 and the mechanism for moving the laser beam source 5 are controlled by a computer device 6.

Where the laser beam touches the surface of the prepolymer 3 according to a pattern determined by the computer device 6, this prepolymer polymerizes. After each coat, the platform 4 is lowered over a distance equal to the thickness of the formed coat. Thus, the object 1 is built layer by layer. However, the object 1 is not formed directly on the platform 4 but on a supporting structure 7 which is first formed in the same manner as the object 1. This or any other supporting structure 7 may extend higher than the bottom face of the object 1 so as to support parts of the object which are situated higher during the formation and in order to prevent deformation of the object.

Characteristic of the invention is that the object 1 is supported by a supporting structure 7, which, instead of being made of solid standing walls crossing one another, has an airier structure.

In the embodiment represented in the FIGS. 2 to 6, support is provided with a supporting structure 7 which comprises vertical walls 8 which are provided with hexagonal openings 9. In order to save a maximum amount of material, the openings 9 are erected such in columns that openings of neighbouring columns are shifted vertically in relation to one another. The walls 8 are erected vertically according to a pattern whereby they are perpendicular to one another and situated at equal distances from one another. The supporting structure 7 is most strong when the openings 9 in the crossing walls are situated such that these walls intersect as much as possible at points where material is present, as is clear from FIG. 3.

Figure 2:
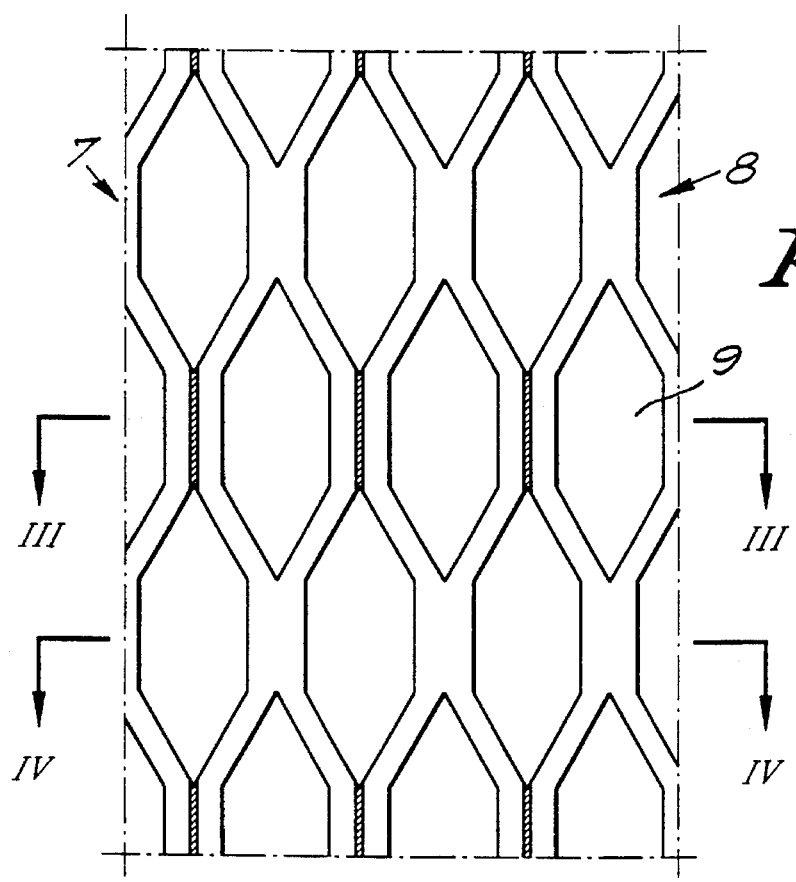
FIG. 2 shows a front view of a supporting structure with which support is provided according to the invention.
Figure 3:
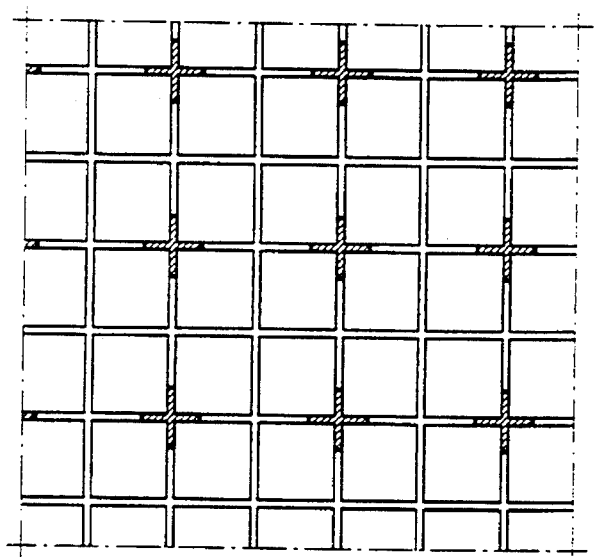
FIG. 3 shows a section according to line III—III from FIG. 2.
Figure 4:
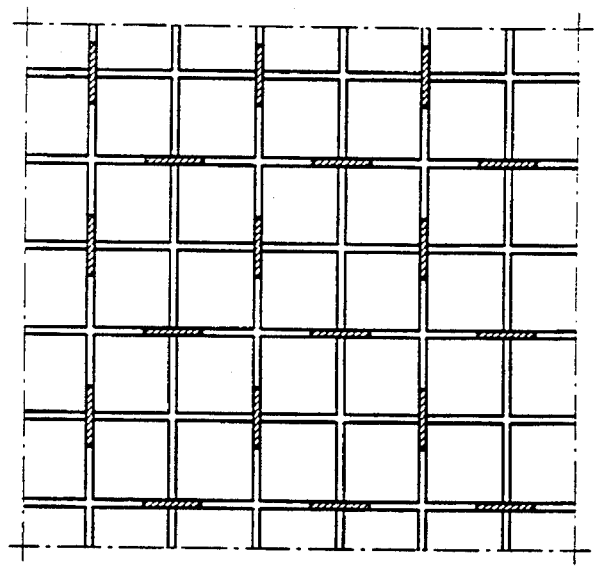
FIG. 4 shows a section according to line IV—IV from FIG. 2.
Figure 5:
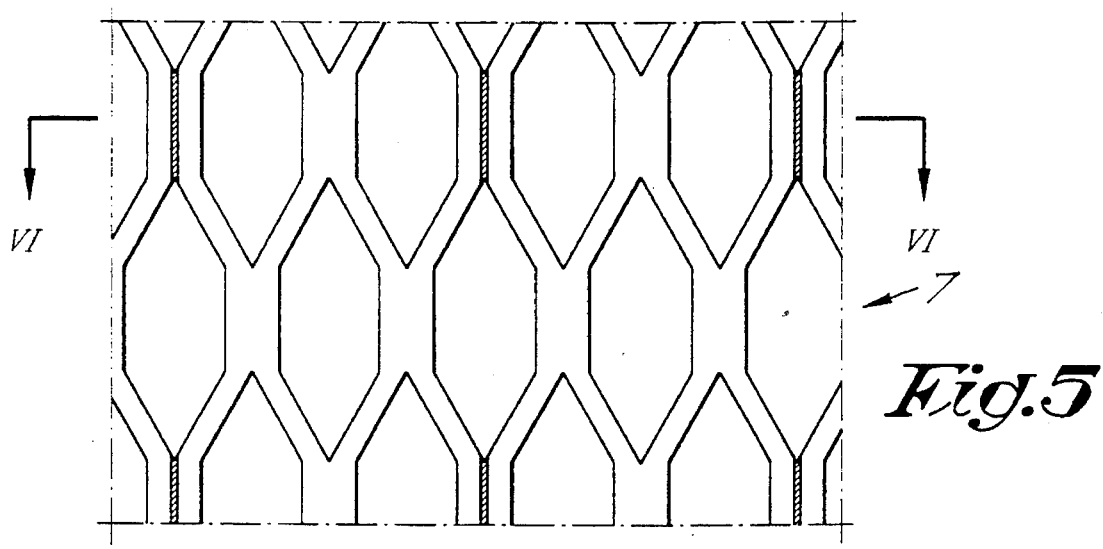
FIG. 5 shows a front view analogous to that in FIG. 2, but with reference to a second embodiment of the supporting structure used to provide support.
Figure 6:
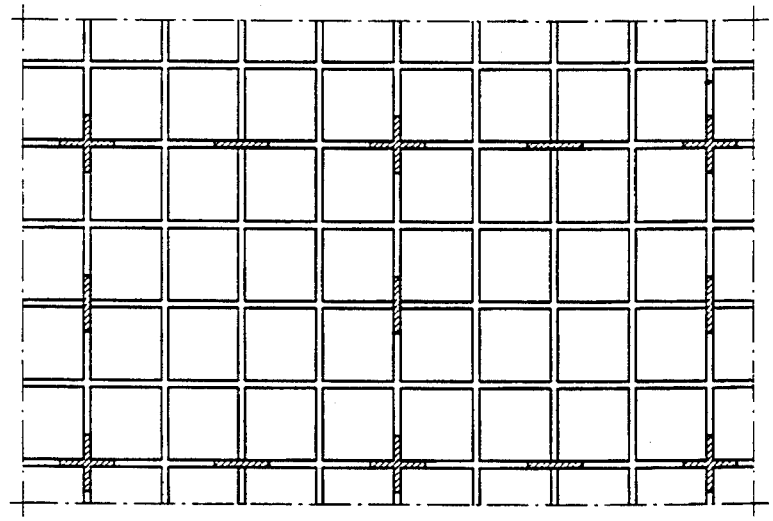
FIG. 6 shows a section according to line VI—VI in FIG. 5.

The difference between the embodiment according to FIGS. 2 to 4 and the embodiment according to FIGS. 5 and 6 resides in the wall thickness, i.e. the number of walls per unit of surface. In the latter embodiment, a wall 8 extends crosswise through every column of openings 9 of a wall 8 perpendicular to it, whereas in the other embodiment, this is only so for every two columns of openings 9.

The openings 9 do not necessarily need to be hexagonal, but can have any shape whatsoever such as the shape of a triangle, a rhomb or a circle.

Figure 7:
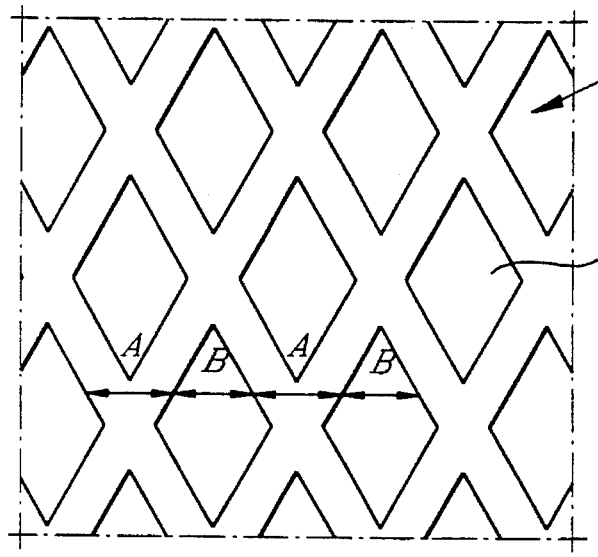
FIG. 7 shows a front view analogous to that in FIGS. 2 and 5, but with reference to a third embodiment of the supporting structure used to provide support.

FIG. 7 shows an embodiment in which the openings 9 have the shape of a rhomb.

Preferably, the openings 9 are provided such that in each coat or horizontal edge of a wall 8 the ratio between the quantity of cured material, indicated by A in FIG. 7 and the interspace, indicated by B in this figure, is identical.

In order to increase the strength of the supporting structure, the standing edges of each of the walls 8 may be free of openings 9. Also the bottom edge of each wall may be free of openings 9 in order to improve the bond of the platform 4 whereas also the top edge of each wall 8 may be free of openings 9 in order to provide a better bond or support for the object 1.

The walls 8 in the spacial supporting structure 7 can also be erected according to other screen patterns than described above. Walls 8 can also be erected in relation to one another at angles other than 90 degrees.

Figure 8:
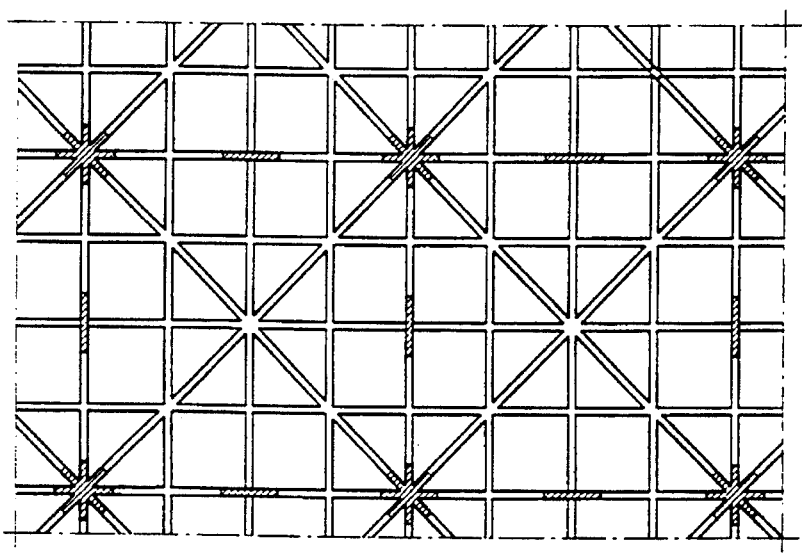
FIG. 8 shows a section analogous to that in FIGS. 4 and 6, but with reference to a fourth embodiment of the supporting structure used to provide support.

FIG. 8 shows an embodiment whereby support is provided with a supporting structure 7 with vertical walls provided with openings 9 which form a lattice pattern. A number of walls 8 are directed perpendicular to one another, so that they form squares in the horizontal section. Other walls 8 are also erected perpendicular to one another, but diagonally in relation to the preceding ones and thus they are directed according to the diagonal lines of the above-mentioned squares.

Other patterns are possible. The walls do not even necessarily need to be flat, but they can be bent both horizontally and vertically. They can be erected vertically or slantingly.

Instead of a large number of openings 9, the walls can be provided with one or a restricted number of openings which are quite large. In one case, only bars remain and the supporting structure 7 is made of bars 11 which are connected to one another in points of junction 12. These bars 11 are built in layers in the same manner as the walls 8.

Figure 9:
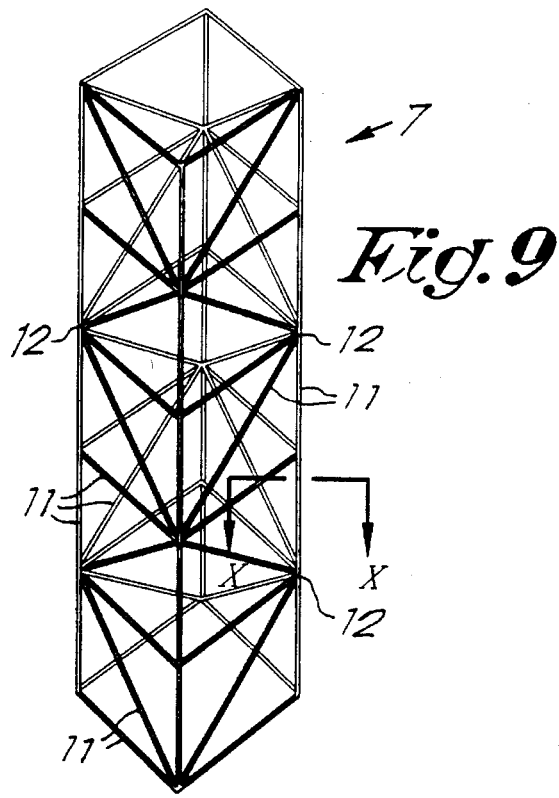
FIG. 9 shows a view in perspective of a supporting structure used to provide support, but with reference to a fifth embodiment of this supporting structure.
Figure 10:
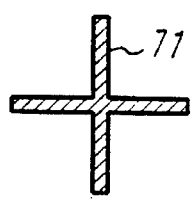
FIG. 10 shows a section according to line X—X from FIG. 9, drawn to a larger scale.

Since only bars remain, it is possible to provide these bars with a profile in their cross section for reasons of strength. FIGS. 9 and 10 show how support is provided with such a supporting structure 7 which is made of bars 11 which are connected to one another in points of junction 12 and which have the shape of a cross in the cross section.

Naturally, the bars can have other sections such as a square, a rectangular, a round or an oval section.

The structure of bars 11 does not necessarily need to have a square base as represented in FIG. 9. This base can also be triangular or hexagonal or it can have other shapes. The bars 11 can be joint to form a lattice structure of great strength.

Figure 11:
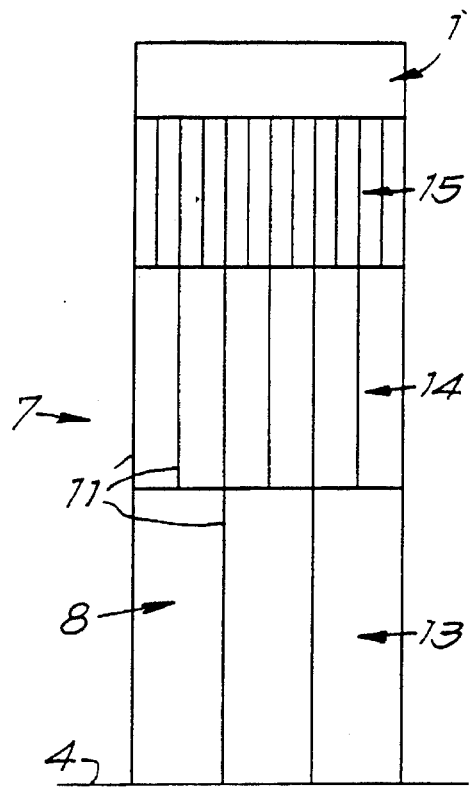
FIGS. 11 and 12 show front views analogous to that in FIG. 2, but with reference to a sixth and seventh embodiment respectively of the supporting structure used to provide support according to the invention and with the supported object.
Figure 12:
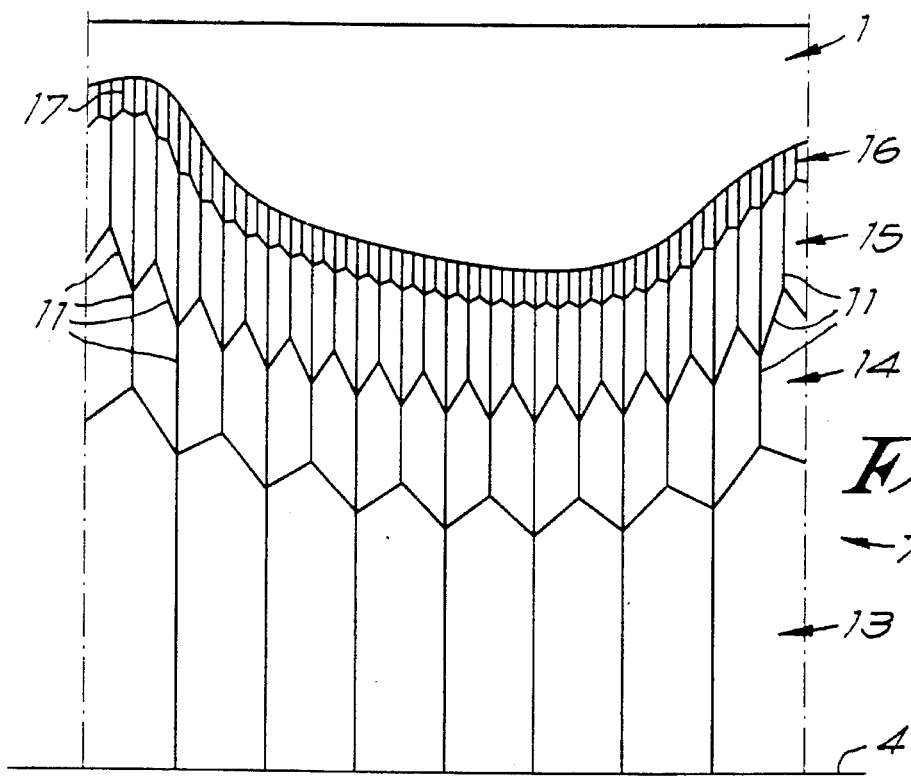

The embodiments according to the FIGS. 11 and 12 differ from the above-described embodiments in that the thickness of the walls 8 or the bars 11, as seen from the horizontal plane, and thus the number of walls 8 or bars 11 of the supporting structure with which support is provided increases towards the top. The object 1 rests on the top side of the supporting structure 7, so that only at this location are a lot of supporting points required, and the supporting structure 7 can be made airy at the bottom against the platform 4 by providing a large distance between the walls 8 or the bars 11. In case walls 8 are used, these can be either or not provided with openings 9.

FIG. 11 shows an embodiment whereby support is provided with vertical walls 8 which are erected according to a specific pattern, for example at right angles in relation to one another. These walls 8 form three different levels 13, 14 and 15. At the lower level 13, which rests on the platform 4, the distance between neighbouring walls 8 is quite large. At the level 14 on top of it, the distance between the walls 8 is half of the previous distance and, as a consequence, there are twice as much walls 8 at this level. At the top level 15, the distance between the vertical walls 8 is once more halved, so that the number of walls at this level is four times greater than the number of walls 8 at the lower level 13.

What is done with the walls 8 can be done in an analogous manner with the bars 11 which can also form different levels with each time more bars at a higher level. FIG. 12 shows such a supporting structure 7 with three levels of bars 11 and with each time a double number of bars at a higher level, whereby moreover the supporting structure 7 has a fourth level 16 on top of the three levels of bars 11 which consists of a very large number of raised rods 17 which form a sort of nail bed which supports the object 1.

Figure 13:
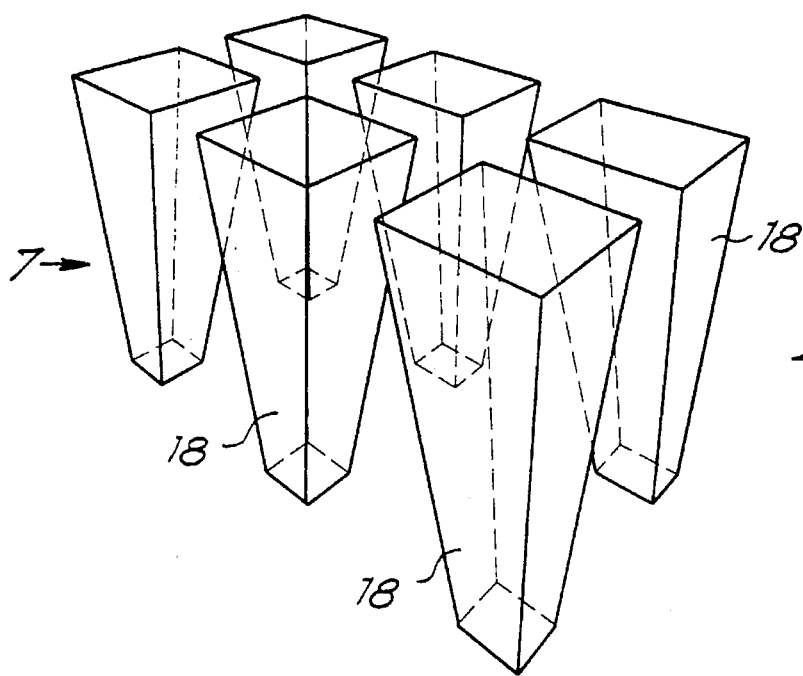
FIG. 13 shows a view in perspective of a supporting structure used to provide support, but with reference to a eighth embodiment of this supporting structure.

The embodiment according to FIG. 13 differs from the above-described embodiments in that the supporting structure 7 which is used to provide support is made of hollow columns 18. These columns 18 can be open or closed at the side. They can have any section whatsoever, for example a square section as represented in FIG. 13. However, they can also be round or have a cross-shaped section. The walls can be provided with openings 9 or have one large opening from top to bottom. In fact, this embodiment can be regarded as a variant on the embodiments according to FIGS. 2 to 8, whereby the openings are very large, however, and extend from top to bottom, so that of the walls 8 only the side walls of the columns 18 remain.

The walls of the columns 18 do not necessarily need to be vertical and the columns 18 must not have the same height over their entire section. In the embodiment according to FIG. 13, the diameter of the columns 18 increases towards the top and thus the columns widen towards the top. As a result, a maximum support is obtained at the top for the object 1, while a minimum amount of material is used at the bottom. Should this be required for stability reasons, the opposite is possible and the columns 18 can widen from the top to the bottom.

Instead of being made of walls, the columns 18 can also be made of bars, which can be regarded as a variant on the embodiment according to FIG. 9, whereby the bar structure is not allowed to continue horizontally, so that columns are formed.

Figure 14:
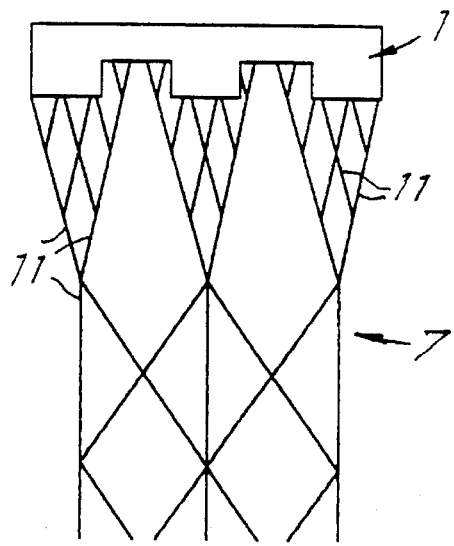
FIGS. 14 and 15 show front views analogous to that in FIG. 2, but with reference to a ninth and tenth embodiment respectively of the supporting structure used to provide support and the supported object.

Such an embodiment is represented in FIG. 14, whereby one or several columns 18 are formed with bars 11 for the support of the object 1, whereby the number of bars 11 is increased towards the top, so that both the bar density and the width of the columns 18 increases towards the top. The bars 11 of each column 18 thus form a tree structure with more branches towards the top.

Figure 15:
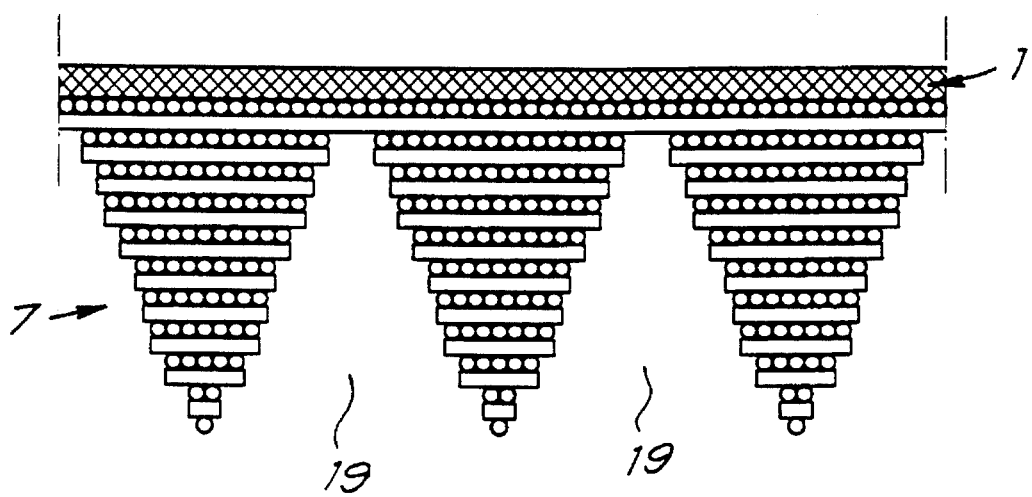

In the embodiment according to FIG. 15, support is provided with a supporting structure 7 which is airy because walls 8 are not formed in each layer. The wall can be alternately formed in one direction and in the direction perpendicular to it. In the first-mentioned direction, several layers can be formed and subsequently several layers can be formed in the other direction. Moreover, large openings 19 can be provided in a thus formed standing wall 8 which extend from the bottom to nearly the top, so that from the supporting structure in fact only columns remain which are airy and widen from the bottom to the top.

It is clear that for supporting one and the same object 1, several independent supporting structures 7 can be built, whereby the different supporting structures can be made according to several of the above-mentioned embodiments. Also, one and the same supporting structure 7 can have several parts or elements which are made according to several of the above-mentioned embodiments.

The above-described supporting structures 7 which are used to provide support to an object 1 are made according to the same techniques which are used to produce the object 1, but whereby special measures are taken so as to obtain the above-described airy structure. In this respect, the control by means of the computer device 6 must be specially adjusted so that for example the openings 9 or 19 can be formed or so that the density of the walls or bars can increase towards the object.

With the help of the computer device 6, the supporting structures 7 can for example be made by means of standard CAD systems which have an interface for rapid prototype production methods, by modelling each wall 8 or bar 11.

A faster production method makes use of programs which automatically design the supporting structures 7 and transcribe them in STL or any other surface format which gives a description of the spacial structure.

The supporting structures 7 can also be obtained on the basis of images, for example provided by a scanner, by logically processing the images. The supporting structures 7 are hereby represented as a set of pixels which will be later converted in a format which is suited for material growth machines such as stereolithography devices.

Another way to make the supporting structures 7 with the help of the computer device 6 consists in logically processing contour lines of the object and by shading the results according to an adjusted methodology.

Therefore, these ways make use of methods which are sufficiently known to the expert.

Another way includes applying an identical method as is used for making the known supporting structures with solid standing walls, for example according to any of the above-described ways, but in combination with a special technique which can be applied with a special software, called Slice software. According to this technique, the slices which will be scanned by the laser beam source 5 are calculated. By hereby providing openings according to a fixed pattern in the vectors which are obtained as the walls 8 are cut, walls 8 are obtained provided with openings 9 or a structure of bars 11 or columns 18. In the case of bars, the required vectors can be added to the remaining vector fragments so as to obtain bars with a specific sectional pattern.

As already mentioned above, the above-described supporting structures 7 are not only obtained by means of stereolithography, but they can also be made by means of other material growth techniques or stratiform production techniques. Especially the embodiments of the supporting structure 7 according to FIGS. 11 and 12 with solid walls can be practically made according to the fused deposition modelling principle.

For the support provided with the above-described supporting structures 7 is required a minimum amount of material. The supporting structures can be made relatively fast. Nevertheless, they can support the object very well. A useful application is found in the production of prototypes, for example on the basis of drawings, or in the medical world to make models of for example bones or prostheses on the basis of scanner images.

We claim:

1. A method of supporting an object made by sterolithography or another rapid prototype production method comprising:

creating at least one supporting structure adapted to support an object to be made with each supporting structure constituting an open framework made up of supporting elements that are interconnected at spaced locations such that each supporting structure has an outer surface provided with openings over a substantial portion thereof.

2. The method according to claim 1, further comprising erecting the supporting elements, which define walls of the supporting structure, with the walls intersecting at spaced locations where each wall includes material.

3. The method according to claim 1, further comprising creating the walls with enlarged openings such that each wall is defined by bars that are interconnected only in junction zones.

4. The method according to claim 3, further comprising widening the bars towards the object.

5. The method according to claim 3, further comprising arranging each of the bars diagonal to an associated longitudinal axis of the supporting structure.

6. The method according to claim 3, further comprising creating a supporting structure wherein at least one edge of a predetermined number of said walls does not have any openings.

7. The method according to claim 1, further comprising arranging the supporting elements farther away from each other near a lower end of the supporting structure than adjacent the object.

8. The method according to claim 1, further comprising providing said supporting structure with plurality of lower supporting elements and, directly under the object, raised rods which support a bottom face of the object.

9. The method according to claim 1, comprising forming the supporting elements as a set of hollow columns.

10. The method according to claim 1, further comprising erecting said supporting elements as columns which widen toward the object.

11. The method according to claim 1, comprising forming the supporting structure of layers or groups of layers which are sequentially formed in a first direction and then in a second direction which is angled with respect to said first direction.

12. The method according to claim 11, comprising forming the supporting structure with said second direction perpendicular to said first direction.

13. The method according to claim 3, further comprising arranging a plurality of said bars transverse to an associated longitudinal axis of the supporting structure.

\* \* \* \* \*